US00PP35221P2

(12) United States Plant Patent
Hansen

(10) Patent No.: US PP35,221 P2
(45) Date of Patent: Jun. 13, 2023

(54) ***HOSTA* PLANT NAMED 'MOUSEKETEER'**

(50) Latin Name: ***Hosta* hybrid (Tratt.)**
Varietal Denomination: Mouseketeer

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 17/803,732

(22) Filed: Nov. 1, 2022

(51) Int. Cl.
*A01H 5/12* (2018.01)
*A01H 6/12* (2018.01)

(52) U.S. Cl.
USPC ..... Plt./353

(58) Field of Classification Search
USPC ..... Plt./263.1, 353
See application file for complete search history.

*Primary Examiner* — Karen M Redden

(57) ABSTRACT

A new and distinct *Hosta* plant named 'Mouseketeer' producing a small-sized upright mound of small leaves that are nearly rounded, lightly cupped, with rounded bases and rounded apices. The leaves are stiff, and smooth, with flat margins and heavy substance. Leaf color is dark green to slightly bluish-green on the wide margins and light yellow in the center with irregular small green flecks and varying shades of light green between the margin and center. The petioles are broad and display the green margin and light yellow center colors. 'Mouseketeer' is useful in the landscape, as a container plant, a specimen or en masse.

1 Drawing Sheet

Botanical classification: *Hosta* hybrid (Tratt.).
Variety denomination: 'Mouseketeer'.

STATEMENT REGARDING PRIOR DISCLOSURES UNDER 37 CFR 1.77(B)(6)

*Hosta* 'Mouseketeer' was first introduced by the inventor as a non-enabling description in registration of the name in early 2021 with the International Cultivar Registration Authority for the genus *Hosta*. No plants of *Hosta* 'Mouseketeer' have been sold in this country or anywhere in the world, nor has any enabling disclosure of the new plant been made.

BACKGROUND AND ORIGIN OF THE PLANT

The present invention relates to a new and distinct *Hosta* plant, *Hosta* 'Mouseketeer' hereinafter also referred to as the new plant or by the cultivar name, 'Mouseketeer'. *Hosta* 'Mouseketeer' was hybridized by the inventor on Jul. 7, 2014 at a wholesale perennial nursery in Zeeland, Mich., USA. The female parent was the proprietary unreleased hybrid known only by the hybrid number H9-273-1 (not patented) and the male parent was 'Dumbo' (not patented). The seeds from this cross were planted in late fall of 2014 and a single seedling selection from this cross eventually produced the new plant. The new plant was assigned the breeder code 14-391-2 and passed the initial evaluation in the summer of 2017. 'Mouseketeer' has been asexually propagated by division at the same nursery since 2019 and also by careful shoot tip plant tissue culture with the resultant asexually propagated plants having retained all the same traits as the original plant. *Hosta* 'Mouseketeer' has been stable and reproduced true to type plants in successive generations of asexual reproduction.

There are over 7,000 registered and established *Hosta* cultivars with The American *Hosta* Society, which is the International Cultivar Registration Authority for the genus *Hosta*. Several of these have blue-green leaf blades. The most similar *Hosta* cultivars known to the applicant with green margins and variegated with creamy centers are: 'Hideko Gowen' (not patented), 'Revolution' (not patented), 'Prestige and Promise' (not patented), 'Pure Heart' (not patented), and 'Spilt Milk' (not patented).

The female parent, H9-273-1, is larger and more arching in habit, larger in foliage size with more acute apices, and shows more separation and intermediate colors between the margin and center. The male parent, 'Dumbo', has a larger habit with larger and solid-green foliage, leaf blades are more cordate with more acute apices, and a slightly sinuate margin.

'Hideko Gowen' has a taller habit with larger leaves that have more vein pairs, a more white leaf center, and lacks the green flecking. 'Revolution' has a taller habit with larger leaves that are more ovate with more acute apices. 'Prestige and Promise' has a larger habit and larger and slightly more ovate foliage that is more chartreuse in the center without the green flecking. 'Pure Heart' has a smaller less upright habit, the foliage is smaller with fewer vein pairs and less green flecking in the center. 'Spilt Milk' has a larger habit with larger foliage with small white flecks in the center of a blue-green leaf.

Other *Hosta* cultivars may have individual traits similar to 'Mouseketeer' but the new plant differs from the above-listed cultivars and all other *Hostas* known to the applicant, by the combination of the following traits:

1. Habit is an upright mound;
2. Leaves are small-sized, nearly rounded, lightly cupped, with rounded bases;
3. Leaves are stiff, smooth, with a flat margin, and heavy substance;
4. Leaf margins are dark green to slightly bluish-green with a bright yellow center;

5. Leaf center has irregular small green flecks and varying shades of light green between the margin and center portions;
6. Leaf petioles are broad and partially flattened showing margin and center colors.

BRIEF DESCRIPTION OF THE DRAWINGS

The drawings of the new plant demonstrate the overall appearance of the new plant, including the unique traits. The colors are as accurate as reasonably possible with color reproductions. Ambient light spectrum, temperature, source and direction may cause the appearance of minor variations in color.

The drawings show a five-year-old 'Mouseketeer' plant in a trial garden at a nursery in Zeeland, Mich. with supplement fertilizer and water as needed.

DETAILED BOTANICAL DESCRIPTION

Figure 1:
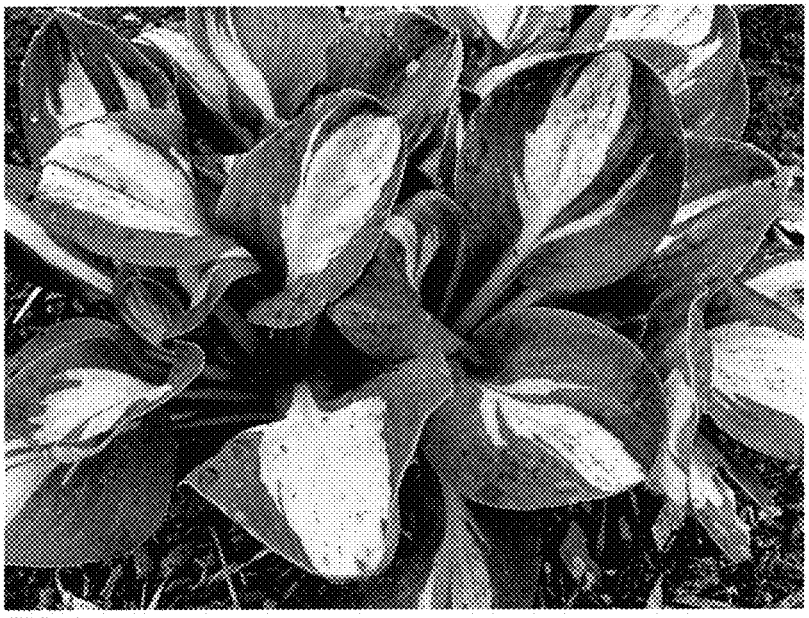
FIG. 1 shows the landscape foliage habit of a new plant prior to flowering.
Figure 2:
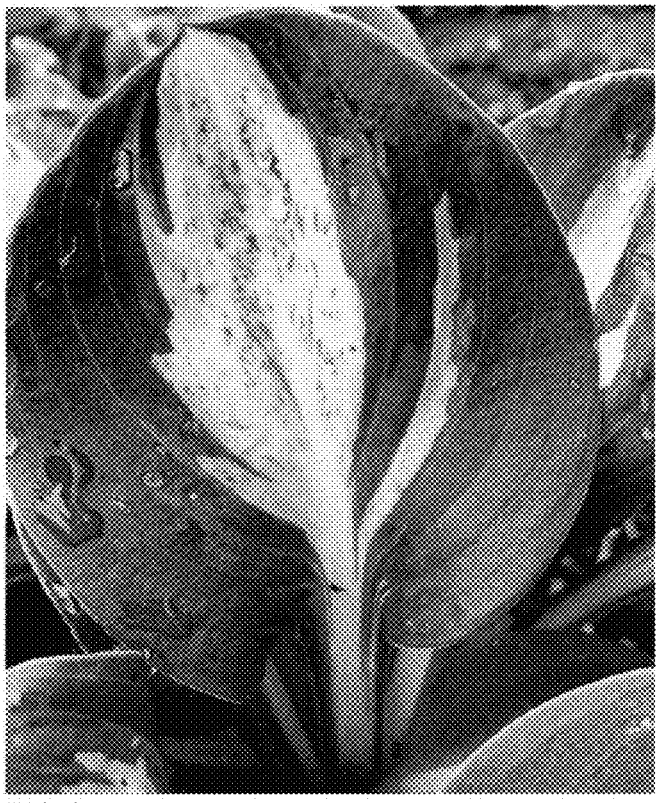
FIG. 2 shows a close-up of a leaf with a portion of the petiole.

The following descriptions and color references are based on the 2015 edition of The Royal Horticultural Society Colour Chart except where common dictionary terms are used. The new plant, *Hosta* 'Mouseketeer', has not been observed under all possible environments. Those skilled in the art will appreciate that certain characteristics will vary with plants that are more mature or plants that are less mature. The phenotype may vary slightly with different environmental conditions, such as temperature, light, fertility, moisture and maturity levels, but without any change in the genotype. The following observations and size descriptions are of a five-year-old plant in a shaded trial garden in Zeeland, Mich. with supplemental water and fertilizer.

Botanical classification: *Hosta* x hybrid;

Parentage: Female or seed parent is a proprietary hybrid H9-273-1; male or pollen parent is 'Dumbo';

Propagation: Garden division and sterile shoot tip tissue culture;

Time to initiate roots from tissue culture: About three weeks;

Growth rate: Moderate to slow;

Crop time: About six months to finish during the spring in a one-liter container from rooted tissue culture plantlet during the warm portion of the growing season;

Rooting habit: Fleshy, lightly branching;

Root color: Nearest RHS NN155C when actively growing depending on growing substrate;

Plant shape and habit: Hardy herbaceous perennial with basal rosette of leaves emerging from rhizomes producing a small-sized mound of upwardly extending petioles and stiff upright leaves;

Plant size: Foliage height to about 23.5 cm above soil line to the top of the leaves, and to about 43.2 cm wide at the widest point about 18 cm above the soil line;

Foliage description: Orbicular; rounded apex; rounded to cordate base; margin entire and flat; slightly cupped; not bullate between the veins; glabrous and smooth both surfaces; adaxial and abaxial slightly glaucous becoming matte; stiff but flexible, not arching or waving with wind; variegated;

Leaf blade size: To about 9.8 cm long and about 10 cm wide about midway from the base; average about 7.2 cm long and 8.0 cm wide;

Variegation dimensions: Margin to 3.3 cm wide, average about 2.3 cm wide; with irregular flecks in the center between 0.5 mm and 13 mm long and 0.5 mm to 1.0 mm across; irregular intermediate zones of 1 mm to 6 mm wide and variable lengths of 2 mm to 50 mm long;

Leaf blade color: Early season and expanding adaxial margin between RHS 137A and RHS N138A, adaxial center nearest RHS 11B with flecks nearest RHS 143A and intermediate zones nearest RHS 144A, and between RHS 192B and RHS N138D; early season and expanding abaxial margin nearest RHS 138A, abaxial center nearest RHS 4D with flecks between RHS 144A and RHS N144A, with intermediate zone nearest RHS 193B and RHS 144A; mid-season and mature adaxial margin nearest RHS 137B, center nearest RHS 155D, with flecks between RHS 137D and RHS 144A, and intermediate zone comprising colors of nearest RHS 143A, RHS 146D, and RHS 192A; abaxial mid-season and mature margin between RHS 146A and RHS 138A, center nearest RHS 155B with flecks nearest RHS 145A, and intermediate zone comprising colors of nearest RHS 145A, RHS 192A, and nearest RHS 146D;

Veins: 9 to 10 pairs with midrib; mostly flat adaxial and costate and smooth abaxial;

Vein color: Young veins in adaxial margin nearest RHS 146A and center region nearest RHS 195B, young abaxial midrib nearest RHS 145D with primary veins nearest RHS 137B in margin portion and in center portion nearest RHS 194A; mature veins in adaxial margin nearest RHS 137B and center nearest RHS 194B, mature veins in abaxial margin nearest RHS 137B and center nearest RHS NN155A;

Petiole: Glabrous and matte both adaxial and abaxial; slightly concavo-convex becoming more flattened distally; stiff; upwardly; to 12.5 cm long, 14 mm wide at base, 20 mm wide below blade, and about 4 mm deep; average about 10 cm long, 12 mm wide at base, 16 mm wide below blade, and 3 mm deep;

Petiole color: Adaxial margin nearest RHS 137A, center nearest RHS 155B with intermediate zone nearest RHS 146C, abaxial margin nearest RHS 138A, and center nearest RHS NN155A;

Inflorescence description: Flowers and buds have not yet been observed;

Fruit and seed: Have not yet been observed;

Disease resistance: No observed resistance to slug feeding. Other resistance to pests (including: *Odocoileus virginianus* and *Oryctotagus cuniculus*) and diseases common to *Hostas* is equal that typical of other cultivars.

Growth: The plant grows best and shows best coloration with plenty of moisture, adequate drainage and light shade, but is able to tolerate some drought when mature.

Hardiness: At least from USDA zone 3 through 8, and other disease resistance is typical of that of other *Hostas*.

It is claimed:

1. A new and distinct *Hosta* plant named 'Mouseketeer' as herein described and illustrated.

* * * * *